(12) United States Patent
Yoshida

(10) Patent No.: US 6,590,166 B2
(45) Date of Patent: Jul. 8, 2003

(54) LIVING BODY VARIABLE MEASURING DEVICE

(75) Inventor: Yoshikazu Yoshida, Tokyo (JP)

(73) Assignee: Tanita Corporation, Tokyo (JP)

( * ) Notice: Subject to any disclaimer, the term of this patent is extended or adjusted under 35 U.S.C. 154(b) by 120 days.

(21) Appl. No.: 09/818,904

(22) Filed: Mar. 28, 2001

(65) Prior Publication Data

US 2001/0032742 A1 Oct. 25, 2001

(30) Foreign Application Priority Data

Apr. 20, 2000 (JP) .......................... 2000-118831

(51) Int. Cl.[7] .................. A61B 5/05; G01G 21/28
(52) U.S. Cl. ................. 177/25.13; 177/25.16; 177/126; 177/238; 177/245; 600/547
(58) Field of Search ............. 177/25.13, 25.16, 177/245, 238–244, 126, 127; 600/547

(56) References Cited

U.S. PATENT DOCUMENTS

| | | | | |
|---|---|---|---|---|
| 4,676,327 A | * | 6/1987 | Luechinger | 177/126 |
| 5,415,176 A | * | 5/1995 | Sato et al. | 177/245 |
| 6,369,337 B1 | * | 4/2002 | Machiyama et al. | 177/25.13 |
| 6,516,221 B1 | * | 2/2003 | Hirouchi et al. | 600/547 |
| 6,516,222 B2 | * | 2/2003 | Fukuda | 600/547 |
| 2001/0007055 A1 | * | 7/2001 | Fukuda | |

FOREIGN PATENT DOCUMENTS

| | | | | |
|---|---|---|---|---|
| JP | 62-28619 | * | 2/1987 | 177/238 |
| JP | 11009569 A | | 1/1999 | |
| JP | 11-094636 | | 4/1999 | |
| JP | 11-128196 | | 5/1999 | |
| JP | 11-128197 | | 5/1999 | |
| JP | 11155829 A | | 6/1999 | |
| JP | 11-332846 | | 12/1999 | |
| JP | 2001-190514 | * | 7/2001 | 600/547 |

* cited by examiner

Primary Examiner—Randy Gibson
(74) Attorney, Agent, or Firm—McDermott, Will & Emery

(57) ABSTRACT

Disclosed is an improvement in a living body variable measuring device comprising a weight scale-like body having electrodes and a weight sensor equipped therewith, and a box-like display device. The electrodes are used in measuring the bioelectrical impedance appearing between both feet. The weight scale-like body has a storage section so sized and shaped as to accommodate the box-like display device.

6 Claims, 4 Drawing Sheets

LIVING BODY VARIABLE MEASURING DEVICE

BACKGROUND OF THE INVENTION

1. Field of the Invention

The present invention relates to a living body variable measuring device capable of measuring the weight and bioelectrical impedance of a person to provide his or her body fat percentage and other pieces of bio-information useful for health maintenance.

2. Prior Art

Recently a variety of living body variable measuring devices for estimating one's body fat percentage and other pieces of bio-information useful for health maintenance have been proposed and practically used. Such pieces of bio-information represent some causes for life-style related diseases. One example of living body variable measuring device is shown in FIG. 4. As shown in the drawing, it is composed of two separate parts, one comprising a weight scale-and-body fat meter combination 26 capable of weighing one's weight and bioelectrical impedance appearing between both feet, and the other comprising a box-like display device 27 connected to the weight scale-and-body fat meter combination 26 by a length of cord 28. This arrangement permits the user to put the display device in front of him while standing upright on the weight scale in stable condition, thus facilitating the watching of the results of measurement. The upright standing posture permits the required measurement with precision.

After use the living body variable measuring device is separated into the weight scale body 26 and the box-like display device 27 to be stored separately. Disadvantageously it may happen that: the weight scale body or the display device cannot be located when the measurement is wanted; the storage space allotted to these separate parts is relatively large; and the length of cord is apt to be caught surrounding objects during measurement.

SUMMARY OF THE INVENTION

In view of the above one object of the present invention is to provide a living body variable measuring device which can be stored in a limited space.

Another object of the present invention is to provide a living body variable measuring device which can be handled with ease.

To attain these objects a living body variable measuring device comprising a weight scale-like body having electrodes and a weight sensor equipped therewith, and a box-like display device, in which measuring device: said electrodes are used in measuring the bioelectrical impedance appearing between both feet; and said weight sensor measures the weight of a person, is improved according to the present invention in that said weight scale-like body has a storage section so sized and shaped as to accommodate said box-like display device.

This arrangement facilitates the storing of the living body variable measuring device as a whole.

The weight scale-like body and the box-like display device may be provided with connection terminals to be mated together for signal communication between the weight scale-like body and the box-like display device. Alternatively the weight scale-like body and the box-like display device may be provided with wireless communication means for signal communication between the weight scale-like body and the box-like display device. This wireless arrangement facilitates the handling of the living body variable measuring device, and a significant reduction of size and weight of the device is permitted.

Other objects and advantages of the present invention will be understood from the following description of living body variable measuring devices according to some preferred embodiments of the present invention, which is shown in accompanying drawings:

FIG. 1a is a perspective view of a living body variable measuring device with the box-like display device separated from the weight-and-bioelectrical impedance measuring composite body according to one embodiment whereas

DESCRIPTION OF PREFERRED EMBODIMENTS

Figure 1A:
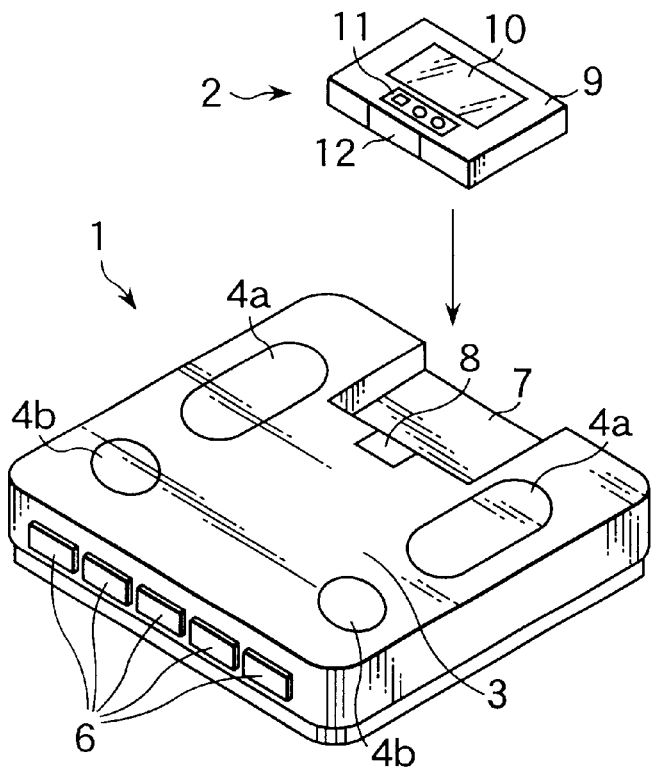
Figure 1B:
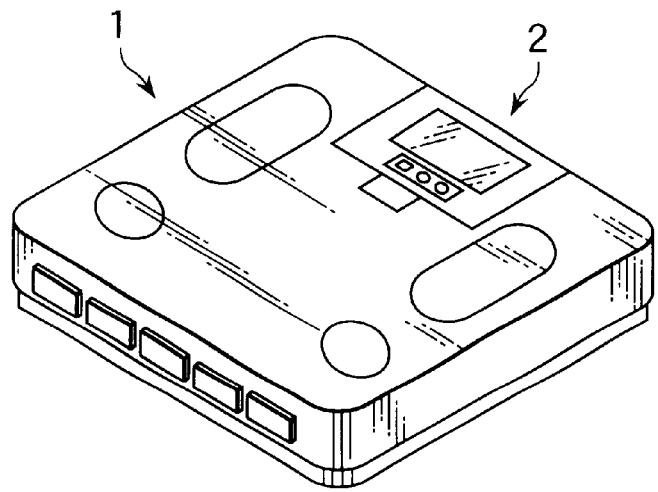
FIG. 1b is a similar perspective view, showing the living body variable measuring device with the box-like display device combined with the composite body.
Figure 2:
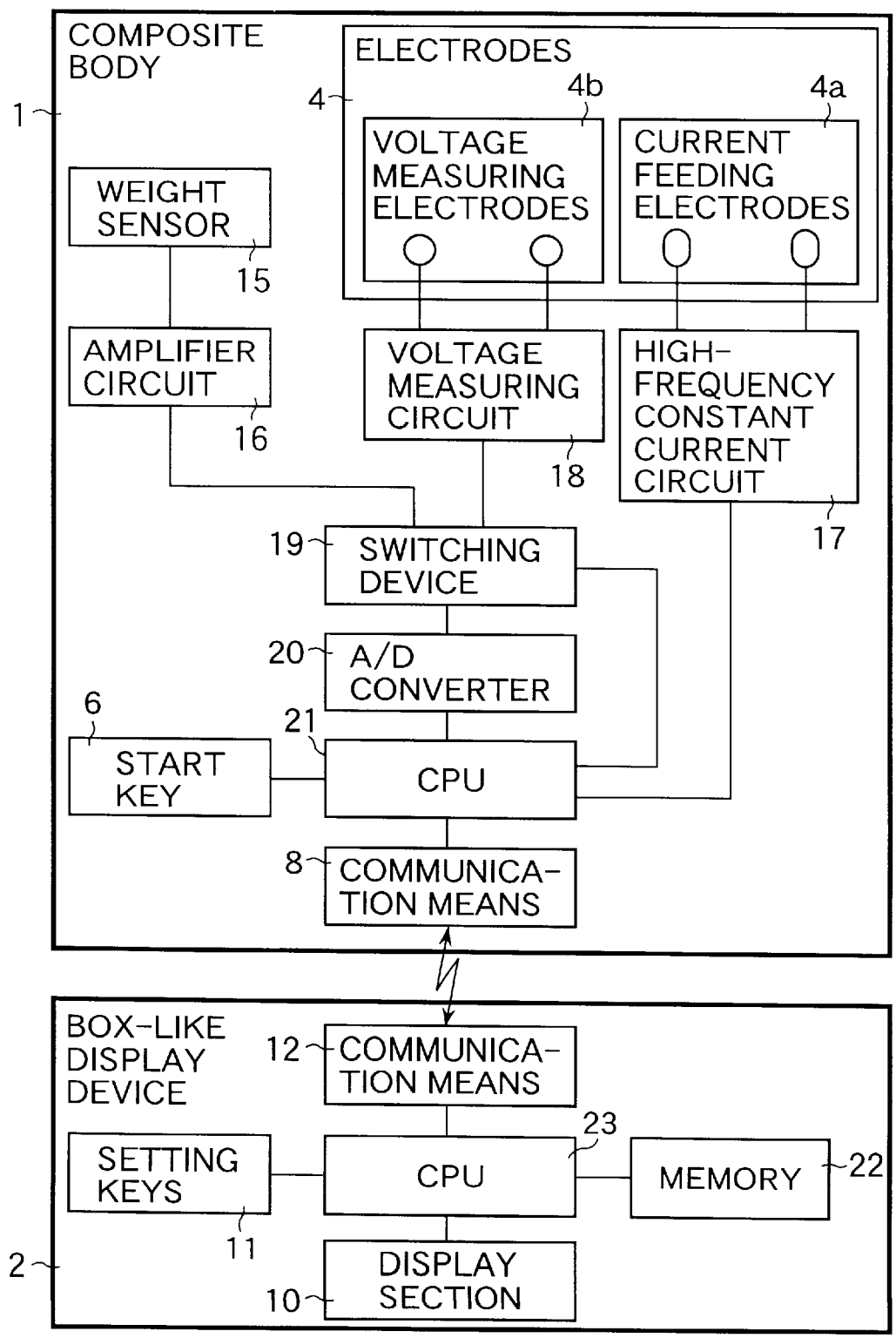
FIG. 2 shows a wiring block diagram of the electric circuit in the living body variable measuring device.

Referring to FIGS. 1 and 2, a living body variable measuring device according to a first embodiment device comprises a weight scale-like composite body 1 and a box-like display device 2. The composite body 1 has electrodes 4a and 4b for use in measuring the bioelectrical impedance appearing between both feet and a weight scale for measuring one's weight. Specifically the weight scale-like composite body 1 has current feeding electrodes 4a and voltage measuring electrodes 4b formed on its top 3, and start keys 6 arranged on its front side. The composite body 1 has a storage section 7 formed on its rear side. The storage section 7 in the form of recess is so sized and shaped as to accommodate the box-like display device 2. As seen from FIG. 1a, infrared signal transmitter and receiver 8 and 12 are provided on the top 3 of the composite body 1 and on the front side of the box-like display device 2 as wireless communication means. The composite body 1 includes a weight sensor 15 for measuring one's weight, a high-frequency constant current circuit 17 for feeding the current feeding electrodes 4a with a weak constant current at a high-frequency, a voltage measuring circuit 18 for measuring the voltage appearing between the voltage measuring electrodes 4b, an amplifier circuit 16 for amplifying signals from the weight sensor 15, a switching device 19 for making a selection between the amplifier circuit 16 and the voltage measuring circuit 18, an analog-to-digital converter 20 for converting analog signals from the voltage measuring circuit 18 or amplifier circuit 16 to digital signals and a CPU 21 for calculating the body fat percentage on the basis of data representing the bioelectrical impedance and weight along with measurement conditions, and effecting measurement and communication controls.

The housing 9 of the box-like display device 2 has a display section 10 and setting keys 11 provided on its top, and an infrared signal communication means 12 provided on its front side. Also, the housing 9 includes a CPU 23 for controlling communication, data storing, displaying and other operations, an associated memory 22.

In use personal data is inputted and recorded with the aid of the setting keys 11, and then, a selected start key 6 is depressed. The person stands on the composite body 1 with his feet put on the current feeding electrodes 4a and voltage measuring electrodes 4b, allowing the results of measurement to be presented in the display section 10. The person can hold the box-like display device 2 with both hands, close to his eyes while the infrared signal communication means 12 is directed toward the counter communication means 8 of the composite body 1. Otherwise, the required measurement can be effected while the box-like display device 2 is put in the storage section 7 of the composite body 1.

As seen from FIG. 1b, the box-like display device 2 can be put in the storage section 7 of the composite body 1, thereby permitting the living body variable measuring device to be stored as a whole.

Use of infrared signal communication between the composite body 1 and the box-like display device 2 permits elimination of the length of cord, accordingly facilitating the handling and storing of the living body variable measuring device. Also, advantageously the box-like display device can be reduced in weight and size, compared with the conventional box-like display device using a length of cord. Wireless communication means other than the infrared communication means may be equally used.

Figure 3:
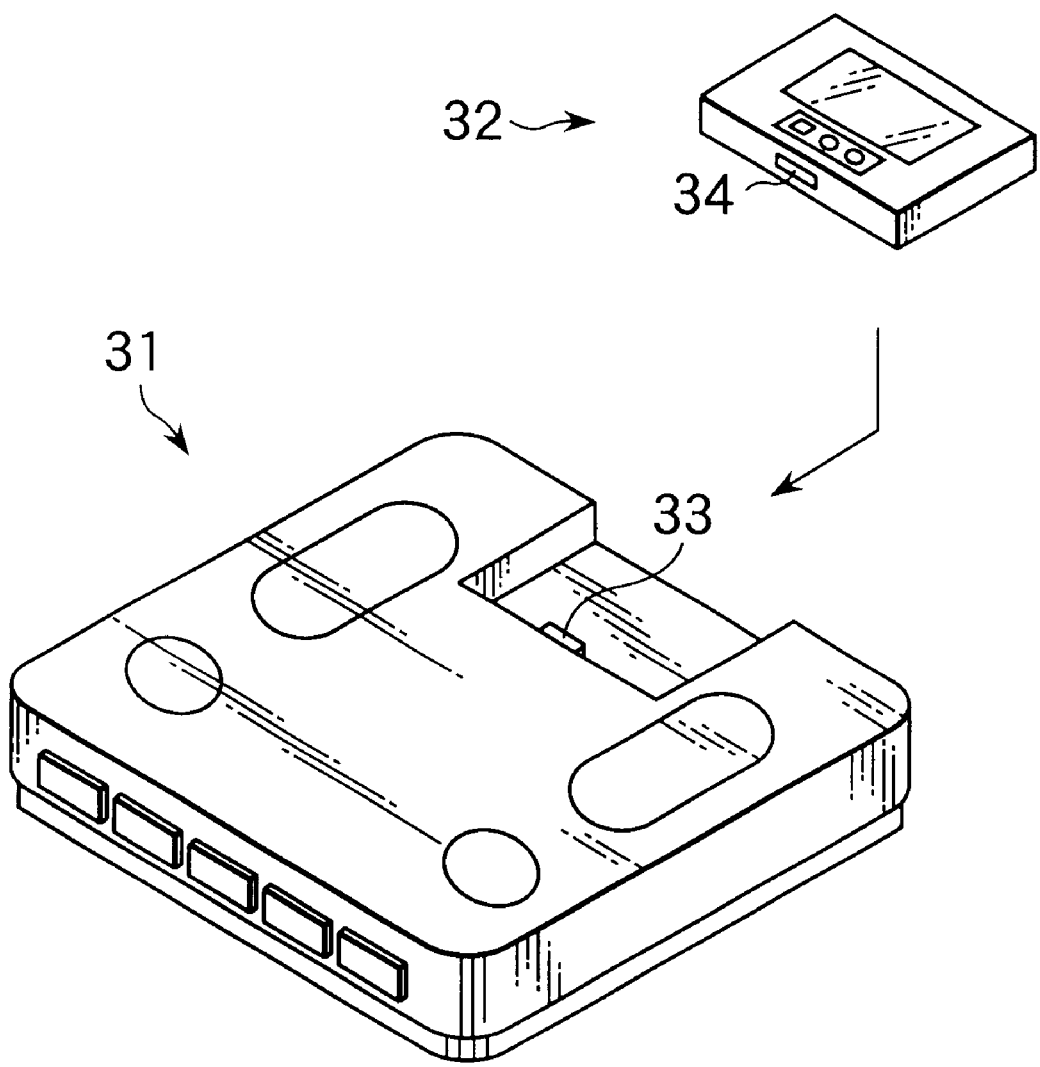
FIG. 3 is a perspective view of a living body variable measuring device with the box-like display device separated from the composite body according to another embodiment.
Figure 4:
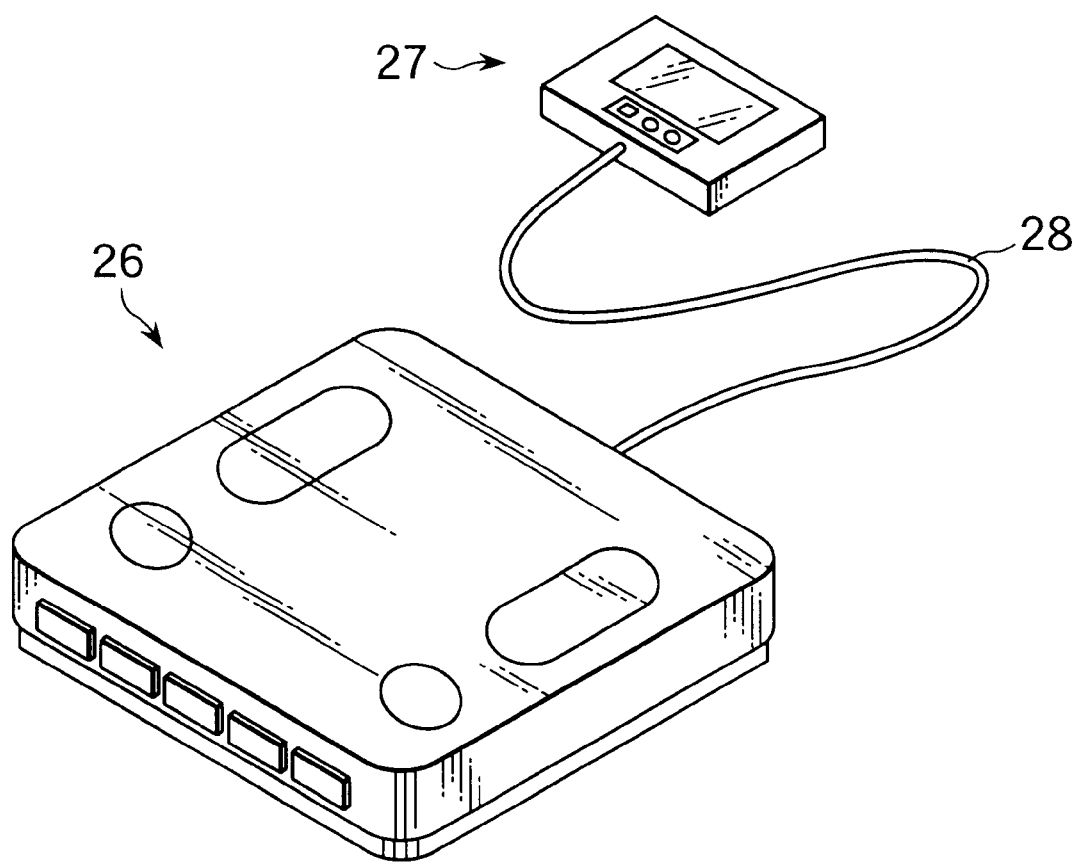
FIG. 4 is a conventional body fat meter-and-weight scale combination.

Referring to FIG. 3, a living body variable measuring device is composed of a composite body 31 and a box-like display device 32 both provided with connection terminals 33 and 34 to be mated together for signal communication. In use a required measurement can be effected with the box-like display device 32 fitted in the storage section of the composite body 31. With this arrangement same advantages as described above may be provided.

The present invention can be equally applied to every kind of living body variable measuring device such as a body water meter or an equilibrium meter, provided that the bioimpedance-and-weight sensor has electrodes provided on its top.

As may be understood from the above, a living body variable measuring device whose box-like display device can be fitted in the storage section of the composite body can be stored as a whole, not separating the box-like display device from the composite body. Thus, it can be stored in a limited space, and there is no fear of either part being not located, which would be caused if these separate parts were stored in different places as is the case with the composite body and the electric cord-and-display device being stored.

Thanks to use of wireless communication means between the composite body and the box-like display device the bother of storing the measuring device of bulky voluminous size and heaviness can be avoided. The measuring device free of the weight of the cord can be handled with ease, and the cordless display device can be put almost everywhere. Combination of such measuring device with a calorie scale or a pedometer will permit collection of extra data useful for health maintenance.

What is claimed is:

1. A living body variable measuring device comprising a composite body having electrodes and a weight sensor equipped therewith, and a display device, in which measuring device: said electrodes are used in measuring the bioelectrical impedance appearing between both feet; and said weight sensor measures the weight of a person, characterized in that said composite body has a storage section so sized and shaped as to accommodate said display device, and said display device is separable from said composite body.

2. A living body variable measuring device according to claim 1 wherein said composite body and said display device are provided with connection terminals to be mated together for signal communication between said composite body and said display device.

3. A living body variable measuring device comprising a composite body having electrodes and a weight sensor equipped therewith, and a display device, in which measuring device said electrodes are used in measuring the bioelectrical impedance appearing between both feet, and said weight sensor measures the weight of a person;

wherein said composite body has a storage section so sized and shaped as to accommodate said display device; and wherein said composite body and said display device are provided with wireless communication means for signal communication between said composite body and said display device.

4. A living body variable measuring device according to claim 2 wherein said electrodes are current feeding electrodes and voltage measuring electrodes; said composite body includes a high-frequency constant current circuit connected to said current feeding electrodes for feeding them with a very weak current of high-frequency, a voltage measuring circuit connected to said voltage measuring electrodes for measuring the voltage appearing therebetween, an amplifier circuit connected to said weight sensor for amplifying the signal representing the weight of the living body, a switching device connected both to said amplifier circuit and to said voltage measuring circuit, an A/D converter connected to said switching device for converting the analog signal from said voltage measuring circuit or said amplifier circuit, and a CPU connected to said A/D converter and to said high-frequency constant current circuit for determining the body fat percentage from the data of bioelectrical impedance and the data of weight, thereby allowing said display device to show the results of measurement via signal communication between said composite body and said display device.

5. A living body variable measuring device according to claim 3 wherein said electrodes are current feeding electrodes and voltage measuring electrodes: said composite body includes a high-frequency constant current circuit connected to said current feeding electrodes for feeding them with a very weak current of high-frequency, a voltage measuring circuit connected to said voltage measuring electrodes for measuring the voltage appearing therebetween, an amplifier circuit connected to said weight sensor for amplifying the signal representing the weight of the living body, a switching device connected both to said amplifier circuit and to said voltage measuring circuit, an A/D converter connected to said switching device for converting the analog signal from said voltage measuring circuit or said amplifier circuit, and a CPU connected to said A/D converter and to said high-frequency constant current circuit for determining the body fat percentage from the data of bio electrical and the data of weight, thereby allowing said display device to show the results of measurement via signal communication between said composite body and said display device.

6. A living body variable measuring device according to claim 1, wherein said composite body has an edge and a box-shaped cutout in the edge to provide said storage section.

* * * * *